(12) United States Patent
Geigle

(10) Patent No.: US 6,352,499 B1
(45) Date of Patent: Mar. 5, 2002

(54) PROCESS FOR OPERATING A BLOOD CENTRIFUGATION UNIT

(76) Inventor: Peter Geigle, In den Muehlgaerten 42, D-63755 Alzenau (DE)

( * ) Notice: Subject to any disclaimer, the term of this patent is extended or adjusted under 35 U.S.C. 154(b) by 0 days.

(21) Appl. No.: 09/297,014
(22) PCT Filed: Oct. 24, 1997
(86) PCT No.: PCT/EP97/05865
  § 371 Date: Apr. 23, 1999
  § 102(e) Date: Apr. 23, 1999
(87) PCT Pub. No.: WO98/18403
  PCT Pub. Date: May 7, 1998

(30) Foreign Application Priority Data

Oct. 25, 1996 (DE) .......................................... 196 44 336

(51) Int. Cl.⁷ .............................................. B04B 11/00
(52) U.S. Cl. ........................................................ 494/37
(58) Field of Search .............................. 494/1, 2, 5, 10, 494/23, 27, 37, 41, 42, 56, 67; 604/4–6; 210/143, 781, 782

(56) References Cited

U.S. PATENT DOCUMENTS

| | | | | |
|---|---|---|---|---|
| 3,409,213 A | * | 11/1963 | Latham, Jr. ................... | 494/41 |
| 3,145,713 A | | 8/1964 | Latham, Jr. | |
| 3,565,330 A | * | 2/1971 | Latham, Jr. | |
| 3,656,685 A | * | 4/1972 | Kjellgren | |
| 4,140,268 A | * | 2/1979 | Lacour | |
| 4,403,604 A | | 9/1983 | Wilkinson et al. | |
| 4,684,361 A | * | 8/1987 | Feldman et al. ............... | 494/41 |
| 4,859,333 A | | 8/1989 | Panzani | |
| 4,879,031 A | | 11/1989 | Panzani | |
| 4,943,273 A | * | 7/1990 | Pages ........................... | 494/41 |
| 4,983,158 A | * | 1/1991 | Headley ......................... | 604/6 |
| 5,045,048 A | * | 9/1991 | Kaleskas et al. ............... | 494/41 |
| 5,100,372 A | * | 3/1992 | Headley ......................... | 494/41 |
| 5,141,486 A | * | 8/1992 | Antwiler ........................ | 494/37 |
| 5,387,174 A | * | 2/1995 | Rochat ........................... | 494/10 |
| 5,405,308 A | * | 4/1995 | Headley ......................... | 494/41 |
| 5,507,779 A | | 4/1996 | Altman | |
| 5,514,070 A | | 5/1996 | Pages | |
| 5,603,337 A | | 2/1997 | Jarvik | |
| 5,607,579 A | * | 3/1997 | Latham, Jr. et al. ............. | 604/4 |
| 5,882,289 A | * | 3/1999 | Sakota et al. .................. | 494/41 |

FOREIGN PATENT DOCUMENTS

| | | | | |
|---|---|---|---|---|
| DE | 2745041 | | 4/1978 | |
| EP | 0014093 | | 8/1980 | |
| JP | 59-69166 | * | 4/1984 | ................ 494/41 |
| WO | WO8000227 | | 7/1979 | |

* cited by examiner

Primary Examiner—Charles E. Cooley
(74) Attorney, Agent, or Firm—Milde, Hoffberg & Macklin, LLP (57) ABSTRACT

A process is disclosed for operating a centrifuging unit with a centrifuging container, in particular a centrifuging bowl, for separating the components of a liquid, in particular blood, containing components with different specific weights. The centrifuging container has a separation chamber, a liquid inlet into the separation chamber. The inlet and the outlet extend through a revolving passage at the upper end of the container. The inlet is in communication with an inlet duct which opens in a defined area of the container into the separation chamber. A pumping device is provided for filling and/or emptying the centrifuging container. The liquid to be centrifuged is supplied through the inlet. After a desired amount is separated, the flow direction between the inlet and the outlet is reversed while the centrifuging container continues to rotate at its full working speed, so that at least one of the separated components is discharged from the separation chamber through the inlet duct and the inlet. The flow direction is then reversed again, so that liquid to be separated is again supplied through the inlet. While the separated component is discharged, a compensating liquid is supplied through the outlet in communication with the separation chamber. Also disclosed is a corresponding centrifuging unit.

7 Claims, 4 Drawing Sheets

PROCESS FOR OPERATING A BLOOD CENTRIFUGATION UNIT

BACKGROUND OF THE INVENTION

The invention describes a process for operating a centrifuging unit, which includes a centrifuging container, in particular a centrifuging bowl, for separating the components of a liquid containing components with different specific weights, specifically blood. The centrifuging container contains a separation chamber, an inlet for the liquid to the separation chamber, and an outlet for a separated component from the separation chamber. The inlet and outlet extend through a revolving passage at the upper end of the container. The inlet is connected to an inlet channel which empties in the lower area of the container into a separation chamber. The unit includes a pump device to fill and/or empty the centrifuging container, whereby the liquid to be centrifuged is led to the inlet.

In addition, the invention has to do with a centrifuging unit, with a centrifuging container, in particular a centrifuging bowl, for separating components of a liquid containing components with different specific weights, specifically blood. The centrifuging container contains a separation chamber, an inlet for the liquid to the separation chamber, and an outlet for a separated component from the separation chamber. The inlet and outlet extend through a revolving passage at the upper end of the container. The inlet is connected to an inlet channel which empties in the lower area of the container into a separation chamber. The unit includes a pump device to fill and/or empty the centrifuging container.

It is the custom to use centrifuging units to separate components of a fluid with differing specific weights. Such centrifuging units, particularly centrifuging bowls, are used in separating blood, to separate the blood into its components. After donation, blood is normally broken down into its main components, i.e., blood plasma, low-molecular substances and proteins, and the cellular elements, of which red blood cells make up the major portion.

It is known that blood is centrifuged in batch fashion using a centrifuging bowl having an admission volume of several hundred milliliters. For each centrifuging process, this centrifuging bowl is filled with blood and centrifuged until the blood components with differing weights have formed layers and have separated from each other in the bowl. Thereafter, when the centrifuging unit has stopped, the individual components are removed from the bowl.

Such previously customary centrifuging permits only the overflow (i.e., the components with the smallest specific weight) to be obtained when the bowl rotates, until it is filled with heavy components. Then the bowl is stopped and once at rest the heavy components are removed from the stationary bowl. If these heavy components are needed (red blood cells erythrocytes- as a rule, in blood centrifuging), then this step presents the obtaining of the end product. Stopping the bowl, emptying it and refilling it, in order to separate several liters of blood into its individual components, is time-consuming.

One centrifuging unit with a bowl of the type mentioned initially for centrifuging blood is known from the U.S. Pat. No. 3,145,713. As depicted in the figures of this publication, the bowl in one embodiment shape is a cylindrical or conical container with an outer annular chamber which is formed between the exterior container wall and an inner insert. By means of a revolving passage on the outer side of the centrifuge container, blood is fed in via an inlet, roughly in the container's rotational axis. From this inlet, a channel leads to the base of the centrifuging container, where the blood, still not separated, is passed into the annular chamber. In the upper part of the annular chamber, provision is made for a connection with an outlet which runs through the revolving passage, by means of which the separated, lighter components are removed. After the annular chamber or separation chamber is filled with the heavy red blood cells separated from the blood, the process of admitting is interrupted, and the rotation of the bowl is stopped. Then the red blood cells are appropriately processed and subjected to deep freezing in the bowl, so that the entire unit with the red blood cells can be stored in deep-freeze fashion. It is necessary to equalize pressure in the centrifuging container between the inlet and outlet. To accomplish this, in the upper area, i.e., in the area where rotation takes place, a connection exists between the inlet area and the outlet area or the separation chamber.

Another centrifuge with a container or a bowl is known from the European Patent No. EP-B1-0 015 288. That text essentially is concerned with the special configuration of the rotating passage in the area of which the inlet and outlet are provided. Also in that bowl, the inlet is run via an inlet channel to the bottom area of the bowl, from which the admitted blood is transferred radially outward via a radial channel into an annular separation chamber. The inlet, placed in the area of the container's axis, is surrounded by an axial annular chamber, leading from the bottom of the bowl to its upper area, where it is short-circuited, i.e., connected, with the outlet or the separation chamber. This connection also serves to equalize pressure between individual chamber areas of the bowl.

Another procedure for separating blood into its components is published in European Patent Application No. EP-A1-0 014 093. The arrangement for carrying out the procedure includes a centrifuge with a rotating basin. In that basin, viewed in the radial direction, two bag-like containers are placed atop each other. Into one of these containers, the blood, not yet separated, is admitted and filled. Following separation, the rotor is stopped and the second container is filled with a liquid. The influx of the liquid into the second container pushes the first component separated from the blood out of the first container.

As the above description of the state of the art shows, and as was already explained, procedures according to the state of the art are carried out in batch fashion, i.e., in each instance, pre-set quantities of blood are processed which match the maximum container filling volume of the centrifuging rotor. Or, the volume of the rotor is used to collect a separated component such as red blood cells. Then the separation chamber, having been filled with these red blood cells, is emptied. Or, this separated component is frozen directly in the centrifuging bowl and stored. If small amounts that are less than the filling volume of such a centrifuging rotor are separated, a danger exists that after the rotor is stopped, the separated component may be mixed with the other separated components.

From the description above it is evident that for separating large quantities of liquid that exceed the filling volume of the centrifuging container, separation into individual batches is necessary, implying multiple starts and stops of the centrifuge, resulting in a time-consuming procedure.

In not only medical technology, but also in biotechnology areas, since separating suspensions using separator bowls by means of gravity gradients results in only slight gravity gradient differences, the liquids to be separated are subject to loads of multiple thousands of g (1 g is simple ground acceleration). Seen in physics terms, in the interior of the separation bowl, the desired gravitational field is created by its rotation. Thus, a centrifugal force F(Z) acts on each particle in the bowl. This force results from the product of the particle's density and the centrifugal acceleration b(z).

The product of the radius r and the angular velocity squared make up centrifugal acceleration b(z).

Classical bowls have the outlet configured as passing via two closely situated, static disks, which act like a pump or like a sliced disk (see aforementioned U.S. Pat. No. 3,145,713, column 5, lines 20 to 32). The liquid column that forms during operation grows with increasing filling until it reaches the outer edges of this pump. Liquid that touches the disks is decelerated and spun inward and can thus exit via the outlet.

The radius r of these disks is in the area of 2 cm. Thus, in a previously customary bowl filled with liquid, a cylindrical inner zone is formed, also having a radius r, which always remains filled with air. Between the surface of the liquid column and the bowl's center of rotation, a pressure difference thus forms which can be computed as P=F/A, with A here being the area.

Working out the formula yields a formula P=D*(2P1*r*n)$^2$. From this the interrelation of rpm, radius and the pressure that results from these is derived, as can be seen in the graph (1).

Most classical bowls are filled by the inlet on the lower end of the bowl's axis of rotation until for example, the separation chamber is filled with a heavy component such as in blood the red blood cells. If this is the case, then rotation of the bowl is halted, the liquid column collapses and then is drained out through the inlet at the foot of the axis of rotation. Here a possible height difference is overcome only by the pump. The volume drained away in the bowl is equalized through air fed through the outlet (see, for example, German Patent Publication No. 27 45 041, page 15, 2nd paragraph, 1st sentence ff.).

With newer bowls an attempt is made to avoid decelerating the bowl by draining them while they are still rotating. This is described in the U.S. Pat. No. 4,879,031. As can be seen from FIG. 1 of this U.S. Pat. No. 4,879,031, the central inlet 11 is made tight against the central channel 6 via seal 14 and 15. Then a subpressure is applied via inlet 11b. The subpressure to be applied must be considerable, since the liquid must be suctioned from a distance that is produced by the axis of rotation (not shown) and a line running parallel to it through the outer circumferential line of disk 13a and 13b. In physics terms, subpressure is limited to 0 bar, the absolute vacuum, and thus to a subpressure of 1 bar in comparison to normal ambient air. Technically, a subpressure that can be generated with normally used roller or peristalsis pumps terminates at about 200 mbar.

Figure 6:
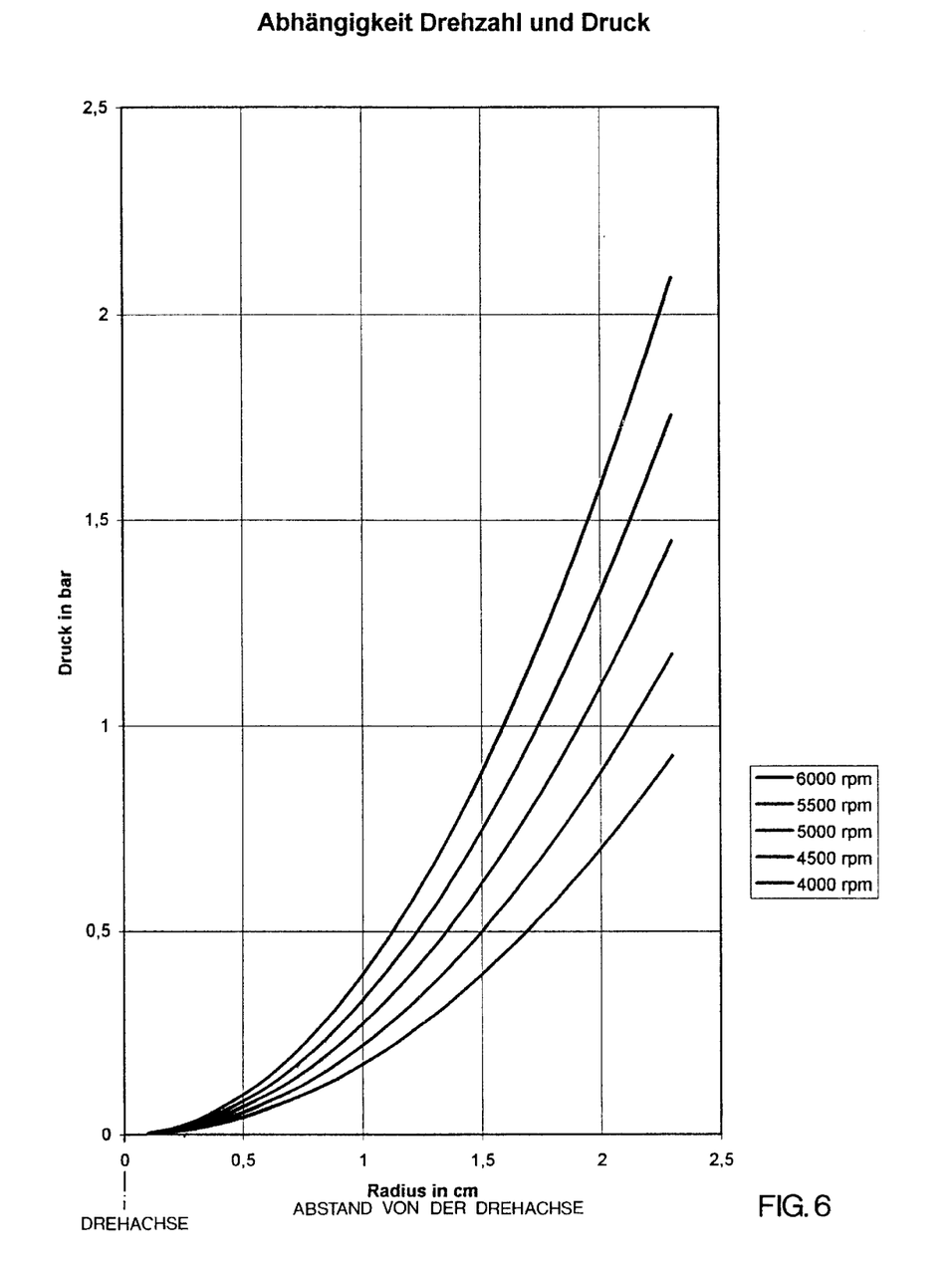
FIG. 6 is a diagram depicting the pressure acting on a particle in a centrifuging container, in dependence on the distance from the rotational axis of the centrifuging container for five different rpm values.

The diagram as per FIG. 6, shows how pressure (in bar) is applied in dependence on the radial distance from the bowl's rotation axis. From this diagram it is evident that at rpms between 4,000 and 8,000—normal for these separation bowls—a suction of the first divided layer at the physical boundary is taking place. In no instance is it possible to suction at the above-named rpm liquids from areas of the bowl that are farther out radially. One remedy could be to further lower the rpm. This, however, could lead to dissolution of the separation boundaries, which would be contrary to the sense and purpose of this patent's bowl. One would achieve the same state as if the bowl had been fully halted. The U.S. Pat. No. 4,859,333 has the same initial conditions as were given above. Here also, suction requires the application of a very high subpressure.

Corresponding to the procedure disclosed in the U.S. Pat. No. 4,859,333 and U.S. Pat. No. 4,879,031, in the first phase of suction, no liquid is required, but rather air, which is located in the center to the degree described above.

Also, it is generally known that cells, particularly red blood cells, are very resistant to pressure. If subpressure is applied, however, they tend toward hemolysis.

The U.S. Pat. No. 5,514,070 shows another option for suctioning liquid from a rotating bowl. As can be seen in the figures, provision is made on the lower end of the inlet 26 for a second pump consisting of two disks with the same radii as disks 30 and 32, which form the classical outlet at the upper end. If the separation chamber is filled with a heavy component—red blood cells, for example, in the case of blood—then via outlet 18, a lighter component such as common salt is fed in (column 2, line 66 ff.). By this means, the heavier components are compressed through passage P2. It is not possible to "back-feed" a heavier component with a lighter component. Therefore, following the principle of linked pipes, the result at minimum will be a dilution. Also, constant sedimentation takes place in annular chamber P3, which is dependent on the sedimentation coefficient. The sedimentation coefficient 3 is normally given in Svedberg units. The sedimentation coefficient 3 is the quotient from the migration speed of particles in the suspension and centrifugal acceleration. It turns out that the migration speed is directly proportional to centrifugal acceleration. This conflicts with the speed at which light liquids are now passed through outlet 18. It stands in a direct relation to the speed at which heavy cells flow through opening E1 into the annular chamber P3. The relation becomes least through the surface of the outlet cross section to the wall surface of annular chamber P3. On the outer diameter of the chamber, the greatest sedimentation rate contrasts with the least flow velocity, directed toward passage P2. By this means, depending on the sedimentation coefficient, the dilution is more or less pronounced.

SUMMARY OF THE INVENTION

The previously described state of the art poses a problem which always arises when quantities of liquids are to be separated that exceed the filling volume of the separation chamber of a centrifuging rotor. It also arises when the filling volume of a separation chamber exceeds that of a separated component. To solve this problem, the present invention provides a process of operating a centrifuging unit. It also provides a centrifuging unit to carry out such a process. Using it, even large quantities of liquids to be separated into at least two components can be broken down without stopping the centrifuge in batch-operation fashion. This also provides a possibility of suctioning out the heaviest components at full operational angular velocity of between ca. 4000 and ca. 6000 rpm. (The operating angular velocity is fundamentally limited at the low end by dissolution of the separation boundaries. At the high end, it is limited by the mechanical loading capacity of the separation bowl.) Suctioning is to be accompanied by the least possible dilution.

In relation to a centrifuging unit of the type initially mentioned, the problem is solved by having the inlet, the feed channel, the separation chamber and the outlet, seen in the direction of flow, become flow paths separated from each other. The pump device, reversing the direction of flow between inlet and outlet, can be switched over to withdraw a separated component via the feed channel and the inlet. The transition between the separation chamber and the outlet is situated closed to the rotational axis, at a distance of at most 10 mm, and preferably 2 to 6 mm away from it.

The process according to the invention makes it possible to remove the separated components and heavy fractions of the centrifuging bowl or centrifuging unit without having to stop the unit from rotating. According to the invention-specific process, a sufficient or pre-set quantity of separated components is concentrated in the centrifuging container. After this has been accomplished, the flow direction that was maintained to feed in the not yet separated liquid (i.e., the flow between the inlet and outlet) is reversed. This is done in order to draw off a separated component via the intake channel, which terminates in defined fashion in an area of the separation chamber. This liquid is then drawn off via the actual inlet, then serving as an outlet, in the area of the centrifuging unit's rotating passage, and expelled outwards. Via the original outlet, as part of removal of the separated component from the separation chamber, a liquid is fed in, in order to fill up the removed volume. This liquid can be a liquid of a type specific to that liquid that was separated. In other words, the new liquid, not yet separated, can be refilled via the outlet, simultaneous with removal of the separated component. Preferably, if blood is being separated, plasma or some other light liquid, such as a common salt solution, should be injected. The separated component is fully withdrawn from the separation chamber. After this is complete, the actual inlet, previously used to remove the separated component, now is employed again to continuously feed in liquid to be separated. This is done until the separation chamber is again occupied by components from the liquid to be separated. Thereafter, the direction of flow, as mentioned above, is reversed again, so that separated components can again be removed. So that the process according to the invention can be implemented in regard to the centrifuging unit, it is essential that the flow paths between the inlet, the intake channel, the separation chamber and the outlet be flow paths that are separated from each other. In other words, only a specified flow of liquid is possible from area to area. Such a centrifuging unit may not have any direct flow connections between inlet and outlet, for example to do any pressure compensations. Otherwise, when flow directions are reversed between feed-in and removal of a separated component, such short-circuit links could permit re-filled liquid for filling the removed volume to flow directly to the outlet and mix with the separated component. Preferably, such a procedure and such a centrifuging unit according to the invention will cause a separated component with a high specific gravity to be removed from the centrifuge. However, it is also possible to have lighter components that are separated from a liquid such as blood to be removed from the separation chamber using the invention-specific procedure. For this, the centrifuging container must have an appropriate shape relative to the centrifuging unit's rotation axis. The feed channel, via which the separated component is to be withdrawn, must terminate in a zone in which the separated component of the fluid to be removed is collected.

The objective is to suction out components from the fluid which possess a high specific weight. To accomplish this, a preferred procedure and a preferred centrifuging unit configuration call for the feed channel to terminate in the bottom area of the centrifuging container. Then the centrifuging unit can be operated long enough to permit essentially the entire separation chamber to be occupied by the specific heavy liquid component which is continuously fed via the feed channel. Meanwhile, the lighter components are expelled via the outlet channel. Only after a sufficient quantity has been collected is the direction of flow again reversed, to feed in the heavy components, while the centrifuging container continues to be rotated. The centrifuging unit is constantly rotating, even during removal of separated components. It will be evident, therefore, that no components get mixed with other components having a different specific weight which are not to be withdrawn immediately.

The following structural details and properties are significant:

Even at full operation rpm, the bowl or centrifuging container is to be completely filled with liquid. The opening of the outlet must begin directly at the wall of the inlet. No pressure differences can then form in a separating bowl completely filled with liquid.

Additionally, inlet channels should be provided whose openings empty as wide as possible on the lower diameter in the separation chamber. These inlet channels should have the smallest possible diameter (ca. 2 to 6 mm, to achieve a high flow velocity during suctioning.

Procedural care is to be taken that the bowl is always filled with liquid, as long as withdrawal at high operational rpm is desired. This means that the liquids or suspension drained out through the opening of the inlet channel and the outlet must simultaneously be replaced by a suitable liquid or suspension via the other inlet or outlet. This ensures that the system will be pressure-free.

When filling commences, the still empty bowl must not be turning at all, or else very slowly. This will have the effect of attaining a complete filling of intake channels. The eddying effect in a centrifugal pump that arises when the bowl is not completely filled will be minimized. However, it may be desired to intentionally induce this effect, for example to suction liquids to be separated out of the vessels, or compensate for pressure losses in the hose systems. This is done by a calculated adaptation of rpm to the desired suction effect.

If the bowl is filled completely or almost completely, the desired operating rpm can be attained. The suspension is divided in according to with the various densities. In blood, for example, the plasma will collect toward the center, while heavier red blood cells move outward. Between these two fractions, the white blood cells and thrombocytes collect as a thin layer.

If blood continues to fill in, the plasma is withdrawn through an overflow channel and the outlet. The bowl can be filled if desired mechanically by devices such as a pump. Or, filling can be done by gravity, by means such as directly via a needle with a suitable hose from a dispenser positioned somewhat higher than the separating bowl.

To automate the procedure, a sensor device is planned, which would detect a certain filling level in the centrifuging container of the component to be separated and then removed. It then issues a pulse which controls the pump device by reversing direction. Preferably, this is an optical device which, in addition, is positioned outside the centrifuging container, and thus does not rotate with it. The pump device initially has fed in liquid to be separated via the inlet. After the above-mentioned full level impulse is emitted, the pump device reverses its direction, to remove the separated component to the centrifuging container via the attachment that normally serves as an inlet. The volume of the separation chamber is a known quantity. Therefore, the amount to be withdrawn, i.e., the amount of the separated component, can be pre-adjusted. This is done so that after the removal of a pre-set, defined volume of separated component, the pump device can again reverse its pumping direction, and again admit liquid to be separated via the inlet.

The intake channel of the centrifuging unit according to the invention is preferably divided into two chambers, with the first section running with its axis along the rotational axis of the centrifuging container. This axis constitutes the neutral zone of the centrifuging unit. For one thing, this arrangement ensures that separation of the not yet separated liquid takes place in the neutral zone, not in the inlet channel; for another, the center of the centrifuging unit's gravity remains by this means on the rotational axis. The second section of the inlet channel can then be in two parts. In other words, on the end of the first section, the second section on opposite sides can be made to branch out radially. If more than two channels are provided, care should always be taken to maintain a certain symmetry, so that the rotation of the centrifuging unit results in no unbalancing. Should only a single feed channel, or a single second section for the feed channel be provided, the radially opposite side should be appropriately weight-balanced. A single feed channel is advantageous in that it is exactly during suctioned withdrawal that a relatively small suctioning cross section is provided. This makes it possible to withdraw as much of the separated component as possible, without collecting additional components.

The aim is to use the volume of the centrifuging container as much as possible for separation. To achieve this, the container is configured so that the separation chamber and the feed channel are separated from each other by a common dividing wall. This means that no additional intermediate space exists between the the feed channel and the separation chamber. The feed channel is designed with a relatively small diameter, in the neighborhood of a few millimeters. However, the overall radial area that surrounds the feed channel, out to the exterior side of the container, is used for the separation chamber. Depending on the components to be separated, the separation chamber is to have a specific shape and orientation to the rotational axis. Preferred is a configuration in which the separation chamber, in its extension in the flow direction to the rotational axis, runs at an incline. This is so that the end toward the outlet is closer to the rotational axis than the passage between the feed channel and the separation chamber. The outlet channel is that channel via which, during operation to separate components, those components are withdrawn which do not remain as separated components in the separation chamber during the separation phase.

Further particulars and features of the invention can be gleaned from the following description of embodiment examples with reference to the drawings.

For a full understanding of the present invention, reference should now be made to the following detailed description of the preferred embodiments of the invention as illustrated in the accompanying drawings.

DESCRIPTION OF THE PREFERRED EMBODIMENTS

The present invention will now be described with reference to FIGS. 1–4 of the drawings. Identical elements in the various figures are identified by the same reference numerals.

Figure 1:
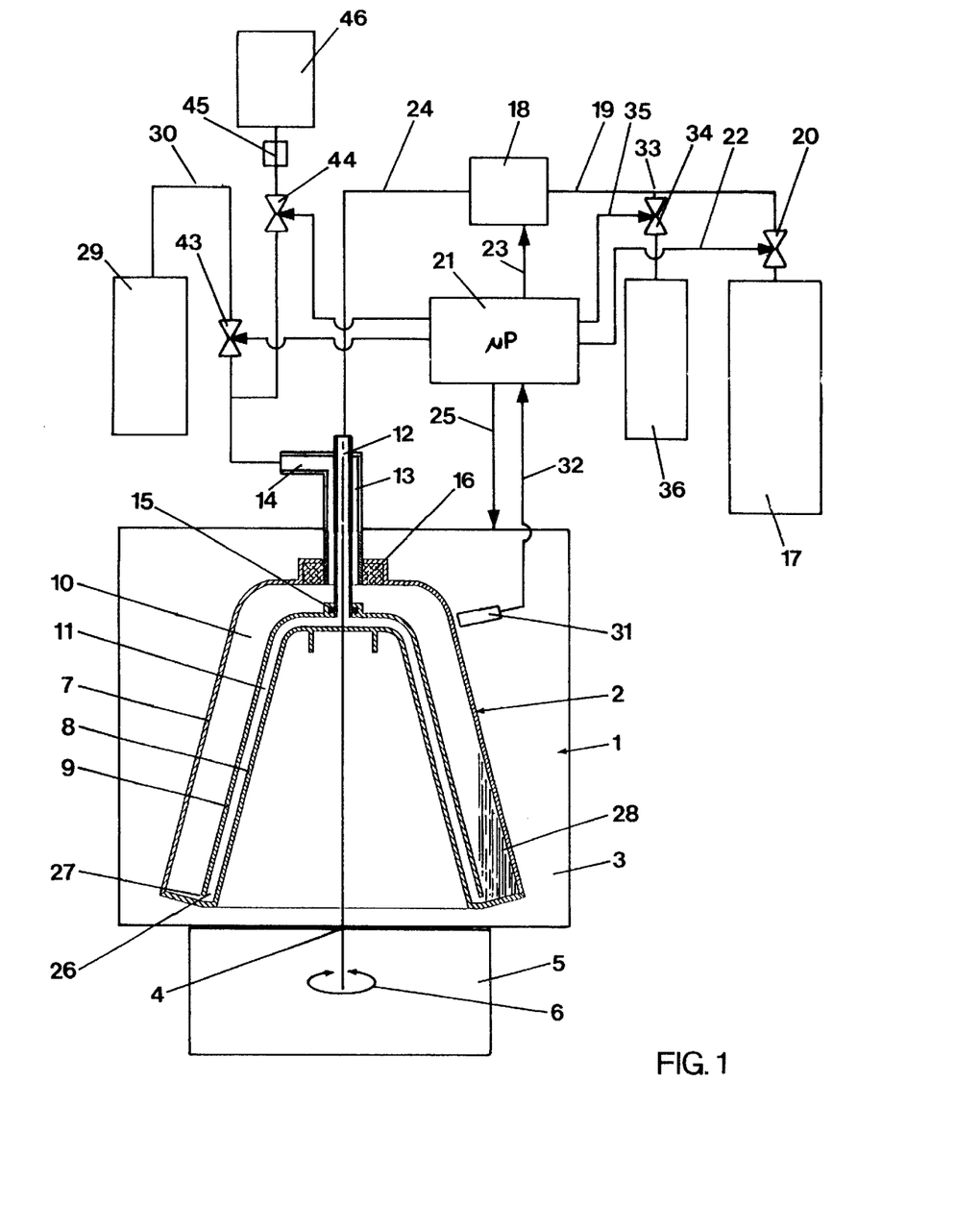
FIG. 1 is a longitudinal section along the rotational axis of a centrifuging unit according to the invention with a centrifuging container. In addition, the pump device, along with the sensor devices and a control unit pertaining to it, are depicted schematically.

The arrangement as depicted schematically in FIG. 1 includes a centrifuging unit 1 with a centrifuging container 2 or centrifuging bowl 2, capable of rotating within a rotary compartment 3 about a rotational axis 4 by means of a drive unit 5 including a motor, as indicated by the rotation arrow 6.

The centrifuging bowl 2 has the exterior shape of a truncated cone, with a truncated cone sheath that forms the outer container wall 7, an additional truncated cone sheath that forms the inner container wall 8, and a truncated cone-shaped insert piece 9 which divides the space between outer container wall 7 and inner container wall 8 into a two chamber section. Viewed in cross section perpendicular to the rotational axis 4, the outer space forms the actual annular-shaped separation chamber 10, while the compartment part between insert part 9 and interior container wall 8 forms an annular compartment which serves as the feed channel 11. As can be seen from the configuration, the separation chamber 10 has a considerably greater cross section perpendicular to rotational axis 4 than the very narrow-designed feed channel 11.

On the top side of centrifuging container 1, a central inlet channel 12 is provided, with its axis running along the rotational axis 4 of the rotor. This inlet channel 12 is connected in flow terms with feed channel 11. The connection point is placed directly in the area close to the rotational axis or turning axis 4. Inlet channel 12 is radially surrounded by a second pipe which forms an outlet channel 13, with an interval that has a lateral connector 14. The connection point between the outlet channel and the separation chamber is likewise placed in the area close to rotational axis 4. This is an advantage in pumping out separated components when the bowl is operating at full rpm, as can be gleaned from FIG. 6. This small interval from inlet channel 12 to outlet channel 13 is attained by making them coaxial in relation to rotational axis 4. Both inlet channel 12 and outlet channel 13 or the appropriate attachment pipes are rotating passages, which remain fixed when centrifuging container 2 rotates, although they provide sufficient sealing via radial seals 15, 16 of separation chamber 10 and feed channel 11 to seal them from the outer environment.

The task is to separate a liquid into its components, i.e., components with varying specific weight. To do this, the liquid is suctioned from a storage container 17 by means of pump 18. An electromagnetically activated cutoff valve 20 is built into the feed line 19, valve 20 being subject to control via a microprocessor 21 with a control line 22. The procedural sequence that controls the centrifuging unit is started via microprocessor 21. Pump 18, via a line 23, is switched on. Simultaneously, valve 20 is opened, so that pump 18 removes liquid such as blood from storage container 17 and feeds it through feed line 24 to entry channel 12, and from there to feed channel 11. Then, if the device for blood separation has been started, feed line 19 can be connected directly to the donor, in which case storage container 17 would be obviated.

At the start of the centrifuging process, the centrifuging bowl can be stationary. However, it is also possible to let the centrifuge rotate at less than the required rpm, as regulated by microprocessor 21 and control line 25.

The liquid from storage container 17 is then brought to the bottom end 26 of feed channel 11, where there is an opening or connection point 27 to separation chamber 10. By way of connection point 27, the delivered liquid enters into separation chamber 10, where the individual components of the delivered liquid form layers outward radially in accordance with their specific weight. Centrifuging bowl 2 and separation chamber 10 have conical or truncated-cone shapes. Due to this, the fraction with the highest specific weight in the delivered liquid will collect in the lower, radially outward-most area of separation chamber 10. In FIG. 1, this area is shown in the lower right side of separation chamber 10 by a shaded area 28. As additional liquid to be separated is fed in from storage container 17, lighter components of the liquid collect closer to rotational axis 4 of centrifugal container 2. These are withdrawn via outlet channel 13 and lateral connector 14. They are directed via outlet line 30 to collector container 29. The connection point 27 should be placed as far as possible outward radially toward the container wall 7, as can be seen in the embodiment shape of the centrifuging container depicted in FIG. 4.

The previously indicated procedure is followed continuously until separation chamber 10 of centrifuging bowl 2 is filled with the specific heavy fraction of liquid. If blood is to be separated into its components, then a defined quantity, i.e., the filled level height of the separated fraction for example red blood cells is detected by a sensor device 31, which may be an optical sensor. A corresponding impulse is transmitted via sensor line 32 to microprocessor 21. If a component separated from the liquid that remains in separation chamber 10 can be distinguished optically from the other components, then sensor device 31 can be an optical detector. It is, however, also possible to use other suitable detectors for this sensor device 31. Sensor device 31 is outside centrifuging container 2, but close to its surface. Normally, such a centrifuging container or centrifuging bowl 2 is manufactured of transparent plastic. To detect various filling amounts in the rotor via this sensor device 31, suitable measures may be taken to maintain the sensor device 31 so it can shift radially, and place it at appropriate heights above the bottom 26 of centrifuging bowl 2.

Microprocessor 21, via sensor line 32, receives appropriate information about attainment of a certain structural height from sensor device 31. After this, with the centrifuging container running at full rpm, feed-in of the liquid from storage container 17 is interrupted. This is done by halting pump 18 and/or closing cutoff valve 20. Then pump 18's direction is reversed, so that inlet channel 12 is now used for suctioning out, allowing the separated component corresponding to shaded surface 28 to be suctioned out via connection opening 27 into feed channel 11, and removed via line 24. These procedures are carried out as the container continues to rotate. In this phase, valve 20 can still remain open, so that the liquid still remaining in channel 12, line 24, pump 18 and line 19 is pumped into storage container 17. When the separated component reaches a branching point 33, cutoff valve 20 is closed via microprocessor 21, and an additional cutoff valve 34, which is linked via a control line 35 with microprocessor 21, is opened. This is done so that the separated component is transferred into a fraction container 36. Removal continues until separation chamber 10 has been emptied of the separated fraction. For this, an additional sensor can be provided which is assigned to the lower area of separation chamber 10. Another option, which is preferred, consists in placing an additional sensor device, not shown in FIG. 1, directly on line 19 before branching point 33. This sensor records when no more fractionated components are located in the line. At this time, regulated via microprocessor 21, cutoff valve 34 is again closed. This ensures that only the fractionated share is transferred into the fraction container 36.

It is evident that when suctioning out the fractionated component from separation chamber 10, compensating liquid from collection container 29 can be fed in via outlet line 30 and outlet 13, to create an appropriate fluid equalization for the fraction withdrawn by inlet 12. However, another liquid can also be fed in via another container which is not depicted.

For the bowl to remain unpressurized, liquid and volume must be equalized.

Purposeful removal or addition of light or heavy components makes it possible in principle to extract each desired fraction of the liquid to be separated, or collect it in the separation bowl.

If a centrifuge constantly operates at the same speed, there will be no velocity difference between the separation chamber and the liquid to be separated. In this case, when the bowl is being filled, the result can be a possible undesired accumulation of still unseparated liquid in the area of outlet 27. To avoid this, outlet 27 can be shaped so that the exiting liquid generates a secondary flow in the separation bowl, and thus a better distribution of the liquid to be separated over the separation chamber is attained.

Such an improved distribution can also be achieved by deceleration and subsequent acceleration of the separation bowl by a few rpm's.

If outlet channel 13 is, as in the present case, situated near the rotational axis or on the rotational axis, then in this area an ever weaker gravitational field is formed. Layering of the liquid to be separated in this area is nullified. To largely prevent the two components that will be separated from getting mixed together, the area between the outer shell 2 and the inner limit 9 in the upper area, down to a distance of about 2 cm from the midpoint, can be designed to be very narrow. Thus, only a very small quantity of liquid will be separated.

After the fractionated component is emptied from separation chamber 20, pump 18's direction is switched again. Cutoff valve 20 is opened and liquid, to be separated again, is passed from storage container 17 via entry channel 11 to separation chamber 10.

The individual processes, i.e. emptying separation chamber 10 followed by centrifuging, until a sufficient quantity of the separated component has again collected in separation chamber 10, can be repeated as often as desired without halting centrifuging container 2 in its rotation. This results in a large time savings; no down times need to be planned between individual emptyings of the separation chamber. On the contrary, separation of even large quantities of liquid needing to be separated can be done in semi-continuous operation.

Along with fraction container 36, additional fraction containers that are not shown can be provided, to fractionate additional components from the liquid to be separated. In such a case, after the entire amount of fluid, or a pre-specified quantity of it, has been separated from storage container 17, the liquid in collection container 29 is again passed to separation chamber 10, in order to separate yet another component from this liquid that has lost the first fraction. The procedure can be carried out in correspondence with that which previously was described: in continuous operation, without stopping the centrifuge.

With the configuration according to FIG. 1, in separating blood, the thrombocytes, for example, can be concentrated in bowl 2, while separation chamber 10 of centrifuging bowl 2 is filled with blood from storage container 17, or directly from the donor, until separation chamber 10 is almost completely filled with the cellular components. The thrombocytes concentrate in the middle of separation chamber 10. In this first filling, the liquid in separation chamber 10 is fed into a bag 29 or 46 attached to outlet channel 13. After further filling of centrifuging bowl 2 or separation chamber 10, plasma overflows the lateral connector 14 and is likewise collected in one of bags 29 or 46. If plasma is the desired product in this procedure, it is collected in bag 29, while air overflows into bag 46. If thrombocytes, for example, are desired, air and plasma are collected in bag 46.

Then, in rotating centrifuging bowls, the erythrocytes are pumped off. If necessary, an additional pump, not shown, can be provided on the outlet side, i.e., attached to lateral connector 14. The volume deficit thus produced is again filled by previously overflowing plasma from bag 46. Thus, centrifuging bowl 2 always remains filled. At the end of this cycle, one has all the thrombocytes of the first cycle, as well as plasma in centrifuging bowl 2 or in separation chamber 10. The next cycle runs similar to the first. Thereafter the thrombocytes of two cycles are obtained in centrifuging bowl 2. When enough thrombocytes have been concentrated in centrifuging bowl 2 after an appropriate number of cycles, the bowl is overfilled with the cells and the thrombocytes are moved in a procedure into the collection bag or vessel 29. For this, a valve 44, assigned to bag 46, is closed. A valve 43, which is assigned to bag 29, is opened. The boundary between the two individual compartments can be additionally regulated via a sensor 45. Only at the end of the procedure, as previously described, is centrifuging bowl 2 stopped and the content returned to the donor. In a stationary condition, the volume deficit in centrifuging bowl 2 is made up for not by plasma, but rather by air from bag 46. Similar to the procedure described, one may also, in separating blood, pump off only the outermost, cleanest erythrocytes.

Figure 2:
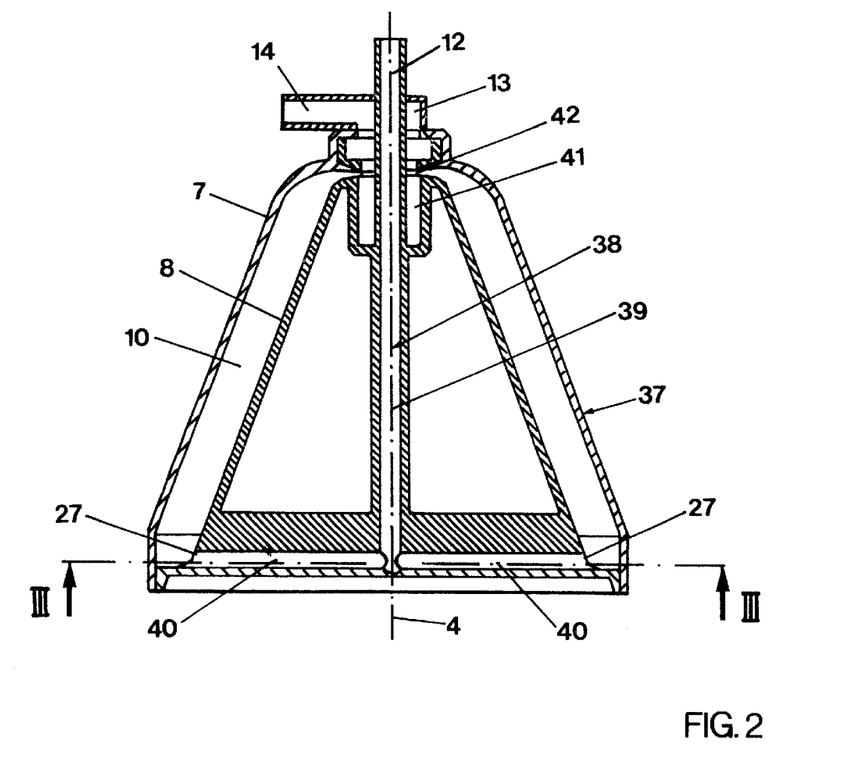
FIG. 2 illustrates another embodiment shape of a centrifuging container.
Figure 3:
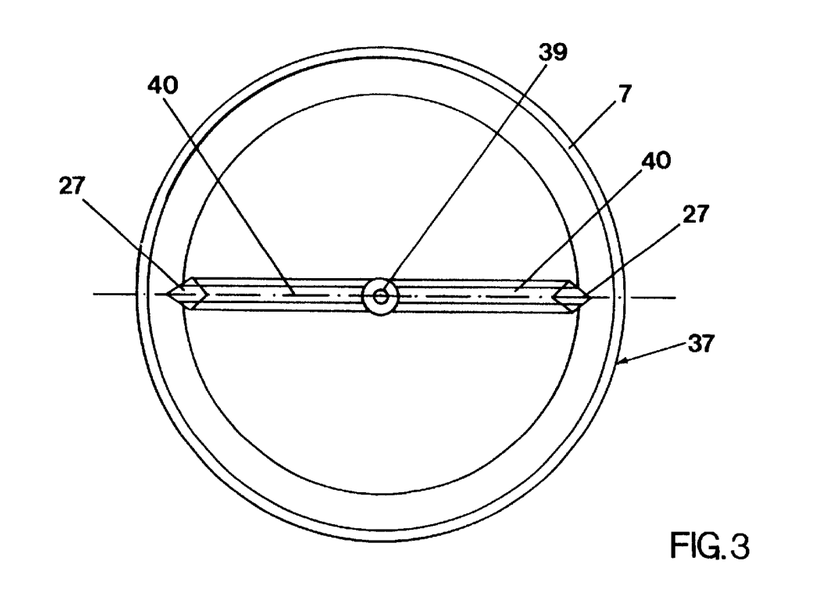
FIG. 3 is a section along section line III—III in FIG. 2.
Figure 4:
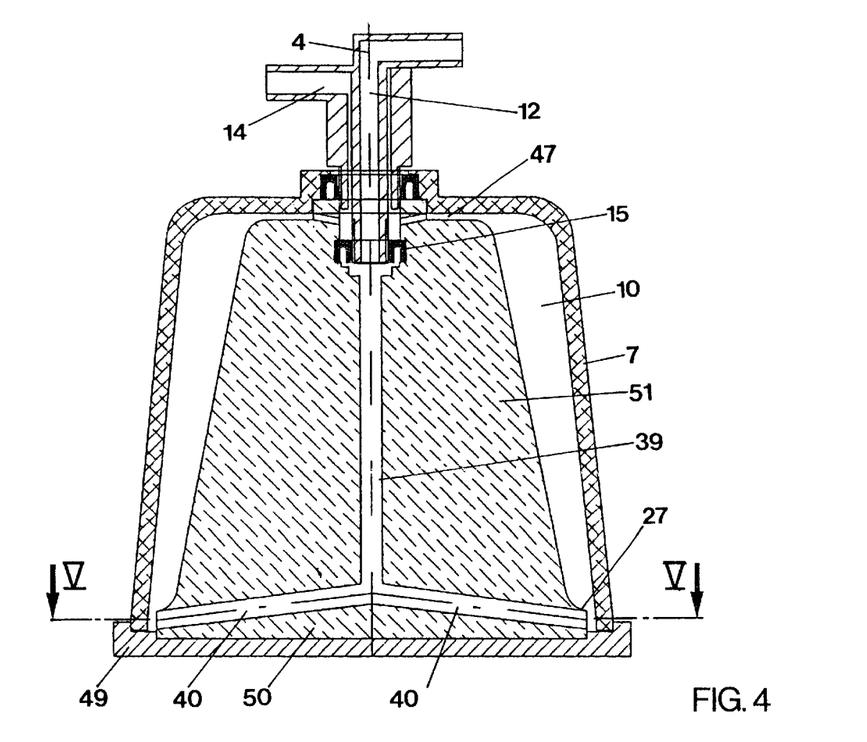
FIG. 4 is a longitudinal section of a third embodiment shape of a centrifuging container.
Figure 5:
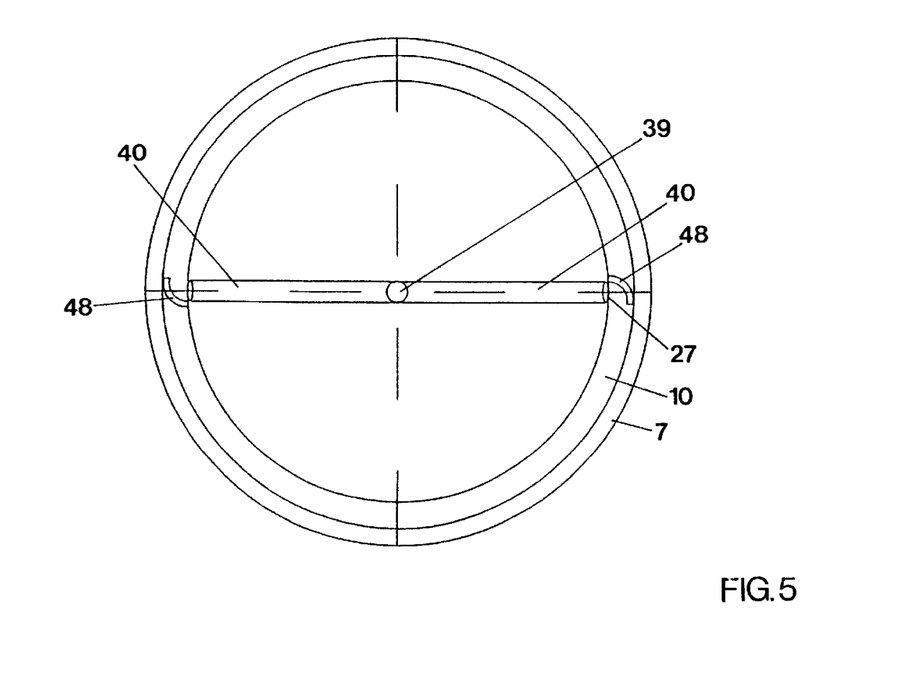
FIG. 5 is a section along section line V—V in FIG. 3.

Two additional embodiment forms of a centrifuging container or a centrifuging bowl are depicted in FIGS. 2 and 3 as well as FIGS. 4 and 5.

The outward shapes of centrifuging bowls according to FIGS. 2 to 5 roughly match centrifuging container 2 as depicted in FIG. 1. As long as parts in FIGS. 2 to 5 are comparable with those of the FIG. 1 embodiment shape, the same reference numbers have been used for such parts as in FIG. 1.

As a comparison between FIG. 1 and FIG. 2 shows, centrifuging container 37 of FIG. 2 does not include insert piece 9 which, parallel to separation chamber 10, limits feed channel 11 on its inner side. Rather, in the FIG. 2 embodiment shape, feed channel 38 is divided into two sections, a first section 39 and a second section 40. The first section 39 runs in extension of rotational axis 4 to the floor of centrifuging container 2. It is at that point that the first section 39 of feed channel 38 makes a transition into two radially opposite sections 40, as can readily be seen in FIG. 3. These radial second sections 40 then pass to connection point 27, which is comparable to connection point 27 of the FIG. 1 embodiment shape. From connection point 27, they then lead to separation channel 10. When compared with the configuration of FIG. 1's feed channel 11, this configuration of feed channel 10 is advantageous in that the inner part that forms the container wall and feed channel 38 can be manufactured from one piece. It is to be noted that in FIG. 2, inlet 12 and channel 38 or 39 are separated via a seal (not shown) which is placed in chamber 41.

In the upper area of centrifuging container 2 of FIG. 2, an expanded area 41 is provided. Into this area 41, transitional openings 42 empty, which connect separation chamber 10 with this expanded area 41 and the outlet channel and the lateral connectors 14. This expanded area 41 serves to admit a lower seal which is not shown.

Separation chamber 10 of centrifugal containers 2 and 37 of FIGS. 1 and 2 should have a volume between 75 and 350 ml, depending on the application.

Centrifuging container 2, corresponding to the FIGS. 2 and 3 embodiment form can be used in centrifuging unit 1, as it is shown in FIG. 1, in place of the centrifuging container 2 shown there. The procedure then is carried out in a way that corresponds to that which was previously explained with reference to FIG. 1.

As already mentioned at the outset, it is possible with the centrifuging containers depicted in the figures to fill the containers even at full operational rpm. This option is especially provided by the fact that the opening of outlet 13 starts directly on the wall of inlet 12, since these are positioned coaxial to each other. Only if the centrifuging container can be completely filled with liquid, particularly at the start of the centrifuging process, is it ensured that no pressure differences appear in the separation bowl 10. Otherwise, a suctioning out of liquid would make this practically impossible. Complete filling of the centrifuging container 2 with liquid is required in order to make possible suctioning out at full operational rpm. Such a complete filling of the centrifuging container with liquid is possible owing to the special configuration of the inlet and outlet directly in the area of axis 4 of the centrifuging container. As shown in the FIG. 2 embodiment form, the upper area of separation chamber 10 has a narrowed cross section and empties directly into outlet channel 13. The cross sectional dimension of this transition 42, viewed in the direction of rotational axis 4, is about 2 mm. But in the FIG. 4 embodiment form, this channel 47 is configured more distinctly, in that its length in the radial direction of rotational axis 4 is about 30 mm. In its basic design, the FIGS. 4 and 5 embodiment form corresponds to the FIG. 2 embodiment form, particularly in regard to the feed channel 38 and the first section 39 and second section 40. It is true that, in contrast to the FIG. 2 embodiment form, the connection point 27 between the second section 40 and the separation chamber is displaced farther radially outward until it is approximately at the outer container wall 7. Between the outlet point from the particular second section 40 and the inner side of outer container wall 7, a distance of only a few millimeters remains. This ensures that even the outer layers of the heavy separated components that collect in this area can be drawn off. Additionally, deflector pieces 48 are provided. They can, for example, be configured like scoops, as shown in FIG. 5. These are provided to impart turbulence to the liquid fed in from section 40 to separation chamber 10. Additionally, in the embodiment of FIG. 4, centrifuging container 7 is closed by a floor 49, in order to form the feed channel 38 in a simple manner. An insert piece 50 is adjoined to floor 49, which forms a part of the second section 40 of feed channel 38, serving as its boundary. Feed channel 38 is situated in an additional insert piece 51. In addition, this insert piece 51 connects the inner container wall 8, which is the boundary for separation chamber 10.

As FIG. 6 shows, the channel configuration as per the FIG. 4 embodiment form is especially good at ensuring that only slight pressures need to be overcome to suction out separated components full rpms. This is due to the small distances of the transition from separation chamber 10 into outlet channel 13. FIG. 6 depicts five curves that relate to different rpm. The lowest curve represents the smallest rpm (4000 rpm), while the top curve represents the highest rpm (6000 rpm).

There has thus been shown and described a novel process for operating a centrifuging unit, and centrifuging unit for carrying out the process which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. Process for operating a centrifuging unit, which includes a centrifuging container for separating the components of a liquid containing components with different specific weights, with the centrifuging container containing a separation chamber, an inlet for the liquid to the separation chamber, and an outlet for a separated component from the separation chamber, with the inlet and outlet extending through a revolving passage at the upper end of the container, with the inlet being connected to a feed channel which empties in a defined area of the container into the separation chamber, and with a pump device to fill and/or empty the centrifuging container, and the liquid to be centrifuged being supplied via the inlet, said process comprising the steps of reversing the direction of flow between the inlet and the outlet, after separation of a desired quantify of a component of the liquid, while rotation of the centrifuging container continues at full rpm, so that at least one of the separated components is drawn off via the feed channel and the inlet from the separation chamber; and thereafter reversing the direction of flow again, so that, via the inlet, liquids to be separated are again supplied to the separation chamber; and, during drawing off of the separated components via the inlet, supplying compensating liquid to the separation chamber via the outlet.

2. Process for operating a centrifuging unit according to claim 1, wherein the liquid is supplied via the feed channel that empties in the lower area of the container into the separation chamber, and after the direction of flow is reversed, separated components with high specific weights are drawn off via the feed channel.

3. Process according to claim 1, wherein switchover of the pump device and thus of the direction of flow between the inlet and outlet is triggered by a sensor device, which detects a certain separated quantity of the heavy components in the separation chamber.

4. Process according to claim 3, wherein detection of the certain separated quantity is done optically.

5. Process according to claim 1, wherein the compensating liquid is one that has a small specific weight compared to the separated components.

6. Process according to claim 5, wherein the liquid to be separated is supplied as the compensating liquid.

7. Process according to claim 1, wherein the liquid to be separated is caused to be turbulent as it flows into the separation chamber.

\* \* \* \* \*